United States Patent [19]

Warriner

[11] Patent Number: Plant 6,666

[45] Date of Patent: Mar. 14, 1989

[54] ROSE PLANT JACSNOW

[75] Inventor: William A. Warriner, Tustin, Calif.

[73] Assignee: Jackson & Perkins Company, Medford, Oreg.

[21] Appl. No.: 84,423

[22] Filed: Aug. 10, 1987

[51] Int. Cl.[4] ..... A01H 5/00

[52] U.S. Cl. ..... Plt./1

[58] Field of Search ..... Plt./1, 23

*Primary Examiner*—Robert E. Bagwill

*Attorney, Agent, or Firm*—Majestic, Gallagher, Parsons & Siebert

[57] ABSTRACT

A rose variety of the shrub class is provided having pure white flowers contrasted by dark green foliage, large stipules and many glands on stipules, peduncles and sepals. This rose variety can be readily propagated as hard or softwood cuttings or by budding.

1 Drawing Sheet

SUMMARY OF THE INVENTION

The present invention relates to a new and distinct variety of rose plant of the shrub class, which was originated by me by crossing the variety Sun Flare, U.S. Plant Pat. No. 5,001, with the variety Simiplicity, U.S. Plant Pat. No. 4,089.

The primary objective of this breeding was to produce a new rose variety of the shrub class. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Presence of large numbers of glands on the peduncles, stipules and sepals;
2. Glossy dark green foliage;
3. Large numbers of clear white flowers;
4. Ability to propagate readily as a hardwood, softwood or budded plant;
5. Large stipules; and
6. Upright vigorous habit of growth.

Asexual reproduction of this new variety by budding and by soft and hardwood cuttings, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jacsnow". Color terminology is in accordance with The Royal Horticultural Society Colour Chart except where an ordinary dictionary significance for the color is apparent.

Observations of the buds and flowers were made from specimens grown in a garden at Irvine, Calif. in July.

Flower

The blooming habit is continuous. The bud size is one and one-quarter to one and one-half inches when the petals start to unfurl. The bud form is pointed ovoid. The bud color when sepals first divide is near White Group 1D; when half blown, the upper side of petals is near White Group 1D and the lower side of petals is near White Group 1D. The sepals have a color near Green Group 138C. The surface texture is covered with fine hairs on the inner surface, edged in glands and the lower surface is covered densely with glands. There are three appendaged sepals lightly to normally appendaged, and two unappendaged sepals with a hairy and glandular edge. The receptacle color is medium green of a funnel shape, medium size and hairy surface. The peduncle is of medium length and has a glandular surface. Peduncle color is medium green and the pendunc le is stiff and erect.

Bloom

Bloom size is medium, with an average open size of three to three and one-half inches, borne singly and several together in clusters. The clusters are rounded to flat. The stems are medium and strong. The form when first open is high center. This form then flattens with the outer petal edges slightly curled. Under normal conditions there are 20 to 25 petals. The upper side of petals is near White Group 1D, as in the reverse side of the petals. The base of petals has a very slight cream-colored spot at the point of attachment with the major color being near White Group 1D. There are no variegations. The general tonality at the end of the first day shows no change in color. At the end of the third day, there remains no discoloration.

The fragrance is slight to moderate. The petal texture is thick, of a deltoid shape. The form is flat with the tips being slightly recurved.

The arrangement is imbricated with few to no petaloids in the center. The blooms drop off cleanly, and last on the plant for a short period and as a cut flower for a short period of time.

Reproductive Parts

The anthers are medium and many, of yellow color arranged regularly around styles. The filaments are white, the pollen is gold yellow, the styles are greenish white, and the stigmas are greenish white.

Plant

A shrub of vigorous, upright growth habit.

Foliage

Medium size, normal in quantity. The new foliage is bronze turning rapidly green, and the old foliage is bright glossy green. Normal mid-stem leaves have five and occasionally seven leaflets.

The leaflets are of an oval pointed shape, are leathery and glossy, and have a serrated edge. The serration is single. Petiole rachis is reddish when young, then green. Stipules are long and edged with glands. The foliage is susceptible to mildew under normal growing conditions at Irvine, Calif.

Wood

New wood is reddish, with a smooth bark. Old wood is green with a smooth bark.

Prickles

There are an ordinary number of prickles on main canes from the base and on laterals from the main canes.

The form is hooked downward. Color when young is green and red.

Small Prickles

There are no small prickles on the main stalks or on the laterals.

Parentage

The seed parent was Sun Flare, U.S. Plant Pat. No. 5,001. The pollen parent was Simplicity, U.S. Plant Pat. No. 4,089.

Classification

Botanical is rosa hybrid and commercial is shrub.

I claim:

1. A new and distinct variety of rose plant and parts thereof of the shrub class substantially as herein shown and described, characterized particularly as to novelty by upright vigorous habit of growth with ease of propagation as hardwood or softwood cuttings or by budding, clear pure white flowers contrasted by dark green foliage, large stipules and the presence of large numbers of glands on stipules, peduncles and sepals.

* * * * *

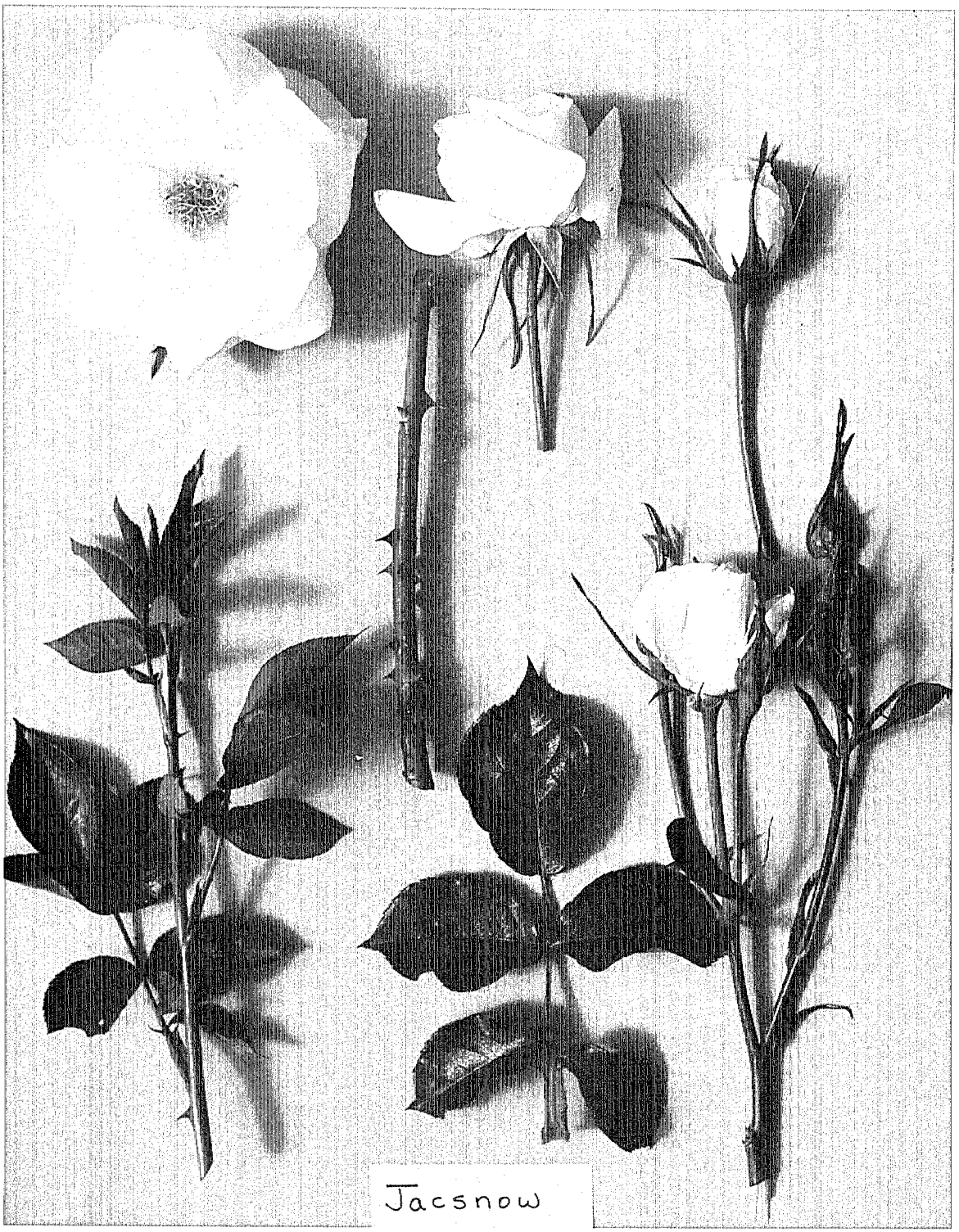
Jacsnow